United States Patent [19]

Reiber

[11] 4,101,961
[45] Jul. 18, 1978

[54] CONTOUR DETECTOR AND DATA ACQUISITION SYSTEM FOR THE LEFT VENTRICULAR OUTLINE

[76] Inventors: James C. Fletcher, Administrator of the National Aeronautics and Space Administration, with respect to an invention of Johan H. C. Reiber, Papendrecht, Netherlands

[21] Appl. No.: 769,148

[22] Filed: Feb. 16, 1977

[51] Int. Cl.² .................. A61B 1/04; H04N 7/02; G06F 15/42
[52] U.S. Cl. ................................ 364/417; 358/96; 358/111; 128/2.05 R
[58] Field of Search .............. 235/151.3; 358/96, 111, 358/139; 444/1; 250/320-323; 128/2.05 R, 2.06 R, DIG. 3; 364/417, 521

[56] References Cited

U.S. PATENT DOCUMENTS

| | | | |
|---|---|---|---|
| 3,361,872 | 1/1968 | Sweeney | 358/96 |
| 3,580,997 | 5/1971 | Milford et al. | 358/111 X |
| 3,869,602 | 3/1975 | Sezaki et al. | 358/111 X |
| 3,988,602 | 10/1976 | Gorsica, Jr. | 235/151.3 X |

*Primary Examiner*—Edward J. Wise
*Attorney, Agent, or Firm*—Darrell Brekke; John R. Manning

[57] ABSTRACT

A real-time contour detector and data acquisition system for an angiographic apparatus having a video scanner for converting an X-ray image of a structure characterized by a change in brightness level compared with its surrounding into video format and displaying the X-ray image in recurring video fields.

The real-time contour detector and data acquisition system includes track and hold circuits adapted to be coupled to the video scanner for sampling the brightness level of predetermined sample points of the current video field in the region of the last detected border point; a reference level analog computer circuit connected to the track and hold circuits and responsive to the sampling of the brightness level of the predetermined sample points for generating a reference brightness level at which the next border point can be detected; and analog compartor connected to the reference level circuit for comparing the brightness level along a video scan line in the current video field with that of the reference brightness level to detect the next border point; a digital processor connected to the comparator and the track and hold circuits and responsive to the detection of a border point for enabling the comparator only within an area of the current video field covered by a narrow expectation window centered about the expected next border position and for determining the sample points to be sampled by the track and hold circuits; a field memory connected to and accessible by the processor for storing the coordinates of the detected border points in the preceding two video fields to partially define the center of the expectation window; and a computer interface connected to the comparators for storing the detected border points in the computer.

8 Claims, 18 Drawing Figures

CONTOUR DETECTOR AND DATA ACQUISITION SYSTEM FOR THE LEFT VENTRICULAR OUTLINE

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention

The present invention relates generally to automatic detection of structures characterized by a change in brightness level compared with its surrounding when the information is carried by a video signal, and more particularly to the automatic detection of the left ventricular contour.

2. Description of the Prior Art

Dynamic measurements of the size and shape of the left ventricular cavity and their correlation with simultaneously occurring pressure and flow events are of great importance in cardiovascular research. Many methods are known for measuring cardiac chamber dimensions and volume in animals and man. However, angiocardiography has proven with time to be the most readily available and reliable method for these purposes. By injecting a suitable radiopaque liquid (usually Renovist) into the left ventricle, a silhouette of the left ventricle can be generated at the face of an image intensifier with X-rays from an X-ray tube underneath the patient. When using the negative of conventional film, the X-ray picture shows the left ventricle as a light structure against a dark background. In the border region between the ventricular silhouette and its background the so-called ventricular contour can be visualized. Certain mathematical methods enable the left ventricular volume to be estimated from this contour data.

The ability to obtain radiographic information concerning chamber size and shape for clinical or investigative use within reasonable periods of time is limited. Presently, the acquisition of such data usually requires the manual tracing of heart outlines to properly define chamber borders, even with films of excellent quality. The use of more advanced or partially automated systems also requires an experienced investigator to define ambiguous areas where the diaphragm or ribs cross the heart outline or the aorta passes behind the heart image. Reproducibility often is poor and the task is tedious because of the great number of pictures to be processed. Since the introduction of the digital computer into the cardiovascular laboratory, many aspects of the data processing have been automated. However, the crucial part in the data acquisition and processing is still the definition and subsequent storage of the chamber borders into the digital computer.

In the last decade, many attempts have been made to automate this procedure and to come up with an automated border recognizer. Most methods are based upon computer processing of the digitized left ventricular image, making online and real-time operation impossible.

An electronic system for automatically detecting structures characterized by a change in brightness level when the information is carried by a video signal and processing the picture information has been discussed in a paper by Leo P. de Jong and Cornelis J. Slager, "Automatic Detection of the Left Ventricular Outline in Angiographs Using Television Signal Processing Techniques", IEEE Transactions on Biomedical Engineering, Vol. BME-22, No. 3, May 1975, pp. 230-237. Starting from the available angiographic data regarding the location and brightness level near an already known contour point of the left ventricle for a given video scanning line, a prediction is made of the most probable location and brightness level of the contour point at the next line. The prediction of location, based on the coherence that may be expected between contour points on successive lines, is realized by defining a so-called expectation window for each subsequent contour point and allowing detection only in this expectation window. Brightness information obtained at sample points near the detected contour is used to predict the reference brightness level at which the next contour point may be detected. This system is principally based on analog circuit design with the expectation and sample-and-hold windows determined by time delays generated by monostable multivibrators which does not permit a relatively easy and accurate correlation of video lines and fields. Its other disadvantages include the following. The center of the expectation window on a given line is defined as having the same horizontal position as the last detected border point on the preceding line. The basic limitations of this principle are that only limited excursions from the direction perpendicular to the video scan lines are allowed and the center of the expectation window is generally not a good approximation of the next border point. The position of the sample point, which is determined shortly before the expected new border position, is also defined with respect to this center of the expectation window. This means that the local direction and movement of the left ventricular outline is not taken into account in the positioning of this sample point, resulting in a less accurate determination of the desired video sample and of the calculated reference level. Only two brightness information sample points are defined for the calculation of the reference level for the next border point to be detected. This does not allow for the determination of the sign of the background slope in the video signal near the actual border; for negative values too high a reference level will be calculated according to the formula for the reference level.

BRIEF SUMMARY OF THE INVENTION

It is therefore one object of the present invention to provide an improved contour detector and data acquisition system.

It is another object to provide such a system based on a digital approach allowing a relatively easy and very accurate correlation of video lines and fields.

It is a further object to provide such a system having potential for online, real-time acquisition of the left ventricular shape during angiocardiography.

The objects of the present invention are achieved by a real-time contour detector and data acquisition system for an angiographic apparatus having video scan means for converting X-ray images of a structure characterized by a change in brightness level compared with its surrounding into video format and displaying the X-ray images in recurring video fields. The real-time contour detector and data acquisition system includes sampling means adapted to be coupled to the video scan means for sampling the brightness level of predetermined sample points of the current video field in the region of the last detected border point; reference level means connected to the sampling means and responsive to the sampling of the brightness level of the predetermined sample points for generating a reference brightness level at which the next border point can be detected; comparator means connected to the reference level means for comparing the brightness level along a video scan line in the current video field with that of the reference brightness level to detect the next border point; processor means connected to the comparator means and the sampling means responsive to the detection of a border point for enabling the comparator means only within a narrow expectation window on the next video scan line centered about the expected next border point and for determining the sample points to be sampled by the sampling means; field memory means connected to and accessible by the processor means for storing the coordinates of the detected border points in the preceding two video fields to partially define the center of the expectation window; and data acquisition means connected to the comparator means for acquiring the detected border points.

The foregoing as well as other objects, features, and advantages of the present invention will become more apparent from the following detailed description taken in conjunction with the appended drawings.

DETAILED DESCRIPTION OF THE PREFERRED EMBODIMENT

Figure 1:
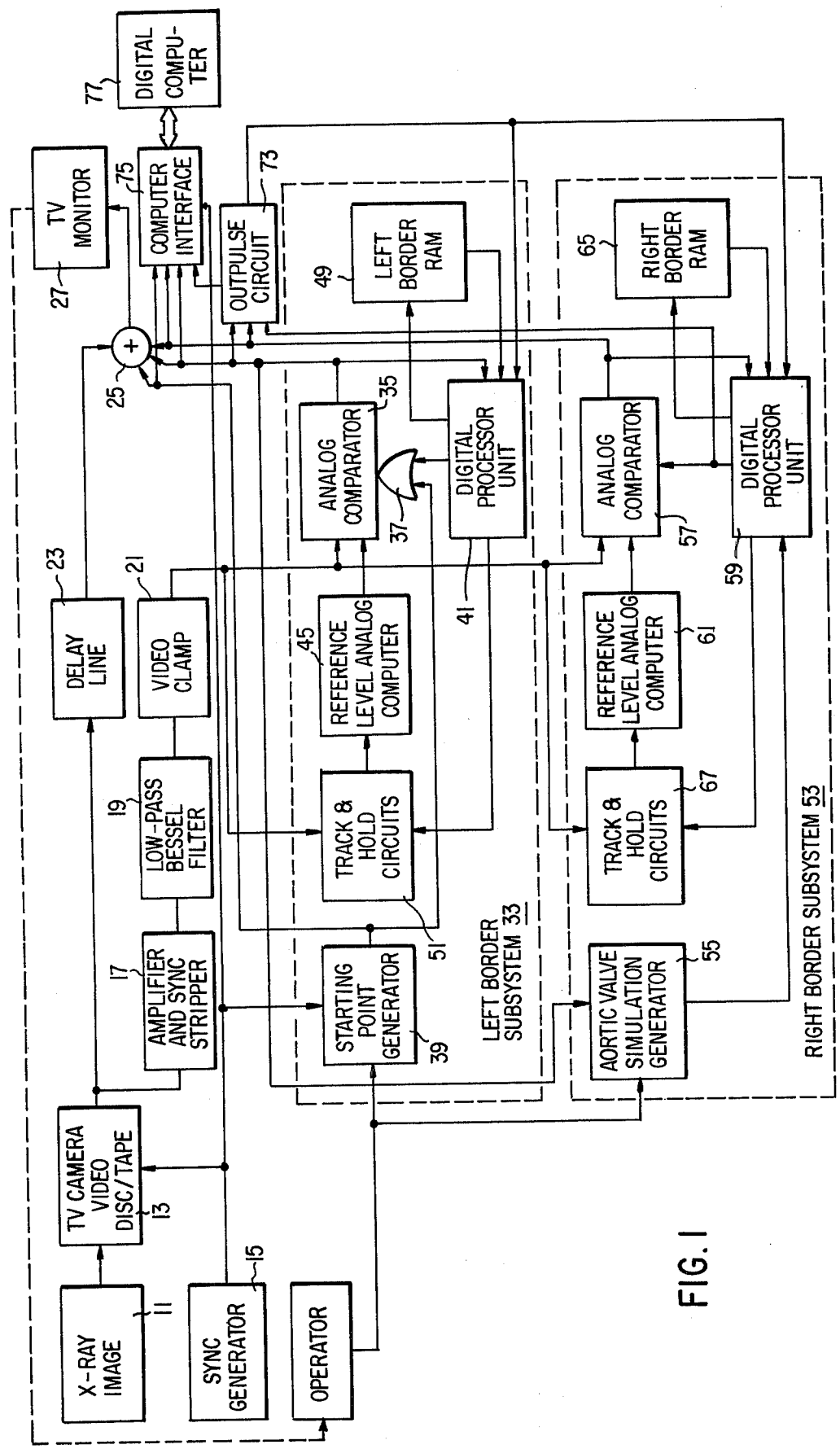
FIG. 1 is a block diagram of the contour detector and data acquisition system of the present invention.

Referring now to the drawings, FIG. 1 illustrates, in block form, the real-time contour detector and data acquisition system for the left ventricular outline of the present invention.

Figure 2:
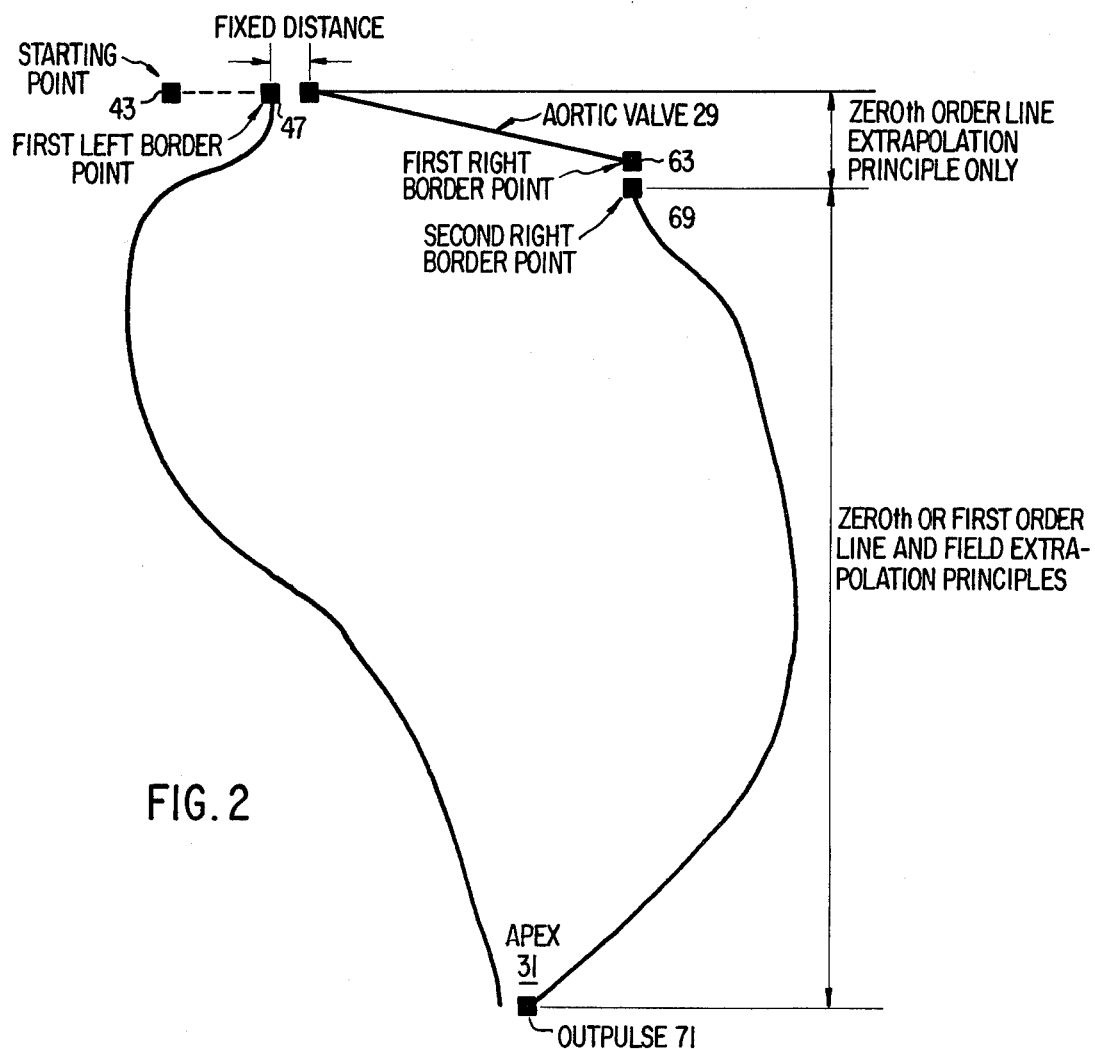
FIG. 2 illustrates the contour of a left ventricular angiogram as determined with the system of the present invention.

FIG. 2 illustrates the contour of the left ventricular outline as determined with the real-time contour detector and data acquisition system of the invention. The X-ray image 11 of the contrast material filled left ventricle is stored for subsequent processing on film (cineangiogram), video tape, or disc. The cineangiogram is converted into video format using a television camera 13. The video signal from either the TV camera, video tape, or disc is the input signal to the system. The required synchronization signals are generated by a sync generator 15. Before any contour algorithm is applied, several pre-processing operations are performed on the input signal to provide for a video signal with an improved signal to noise ratio and a restored DC level. The signal is amplified, and sync pulses which are present in the video signal are stripped off in an amplifier and sync stripper 17. Next, a 1 MHz, low-pass Bessel function filter 19 suppresses the upper frequencies which do not contain relevant contour information. The filtered signal is then clamped for DC level restoration in a video clamp 21. For display and visual feedback, the input video signal is also passed through a delay line 23 which equalizes the total delay of the low-pass filter and the logic circuitry involved in the contour detection. The delayed signal is then applied to a summation amplifier 25 where the detected contour pulses are mixed into the video signal with the correct time relation. The total video signal is the output signal of the system and is used to display the X-ray image with the detected border on the TV monitor 27.

The rest of the system is divided into two almost identical subsystems, one for the left border and one for the right border. Referring to FIG. 2, in this context, left and right are defined with respect to the chord from the left hand side of the designated aortic valve 29 plane to the apex 31 of the left ventricle, as viewed on the screen of the TV monitor 27.

The left border subsystem 33 will now be described. An analog comparator 35 has a control input fed by a two-input OR gate 37. A starting point generator 39 is connected to one input of the OR gate and a digital processor unit 41 is connected to the other input of the OR gate. The analog comparator 35 is enabled for the first time during a video field at a starting point 43 generated by the starting point generator 39. This starting point 43 can be manually positioned by the operator arbitrarily over the screen of the TV monitor 27, but is usually positioned at the aortic valve 29 plane. As soon as the video signal which is fed to the analog comparator 35 from the video clamp 21 reaches a reference level supplied from the dynamic reference level analog computer circuit 45 and preset by the operator, the first left border point 47 is detected. As the comparator 35 changes state, a narrow pulse is fed to the summation amplifier 25, where it is mixed into the video signal for visual feedback purposes.

Figure 10:
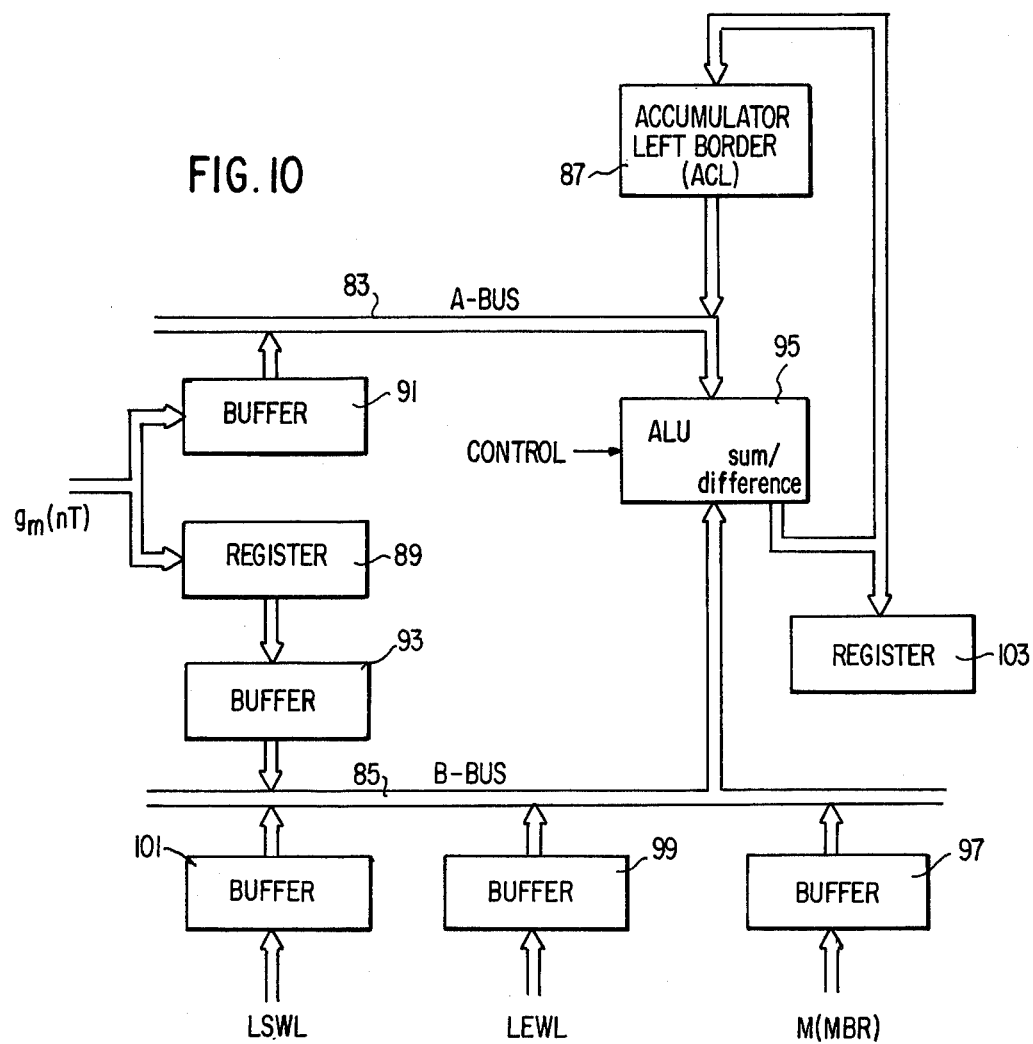
FIG. 10 is a block diagram for explaining the manner in which the center of the expectation window is calculated by the line and field extrapolation methods, as well as the sample and expectation points LSPL1 and LEPL, respectively for the left border.
Figure 11:
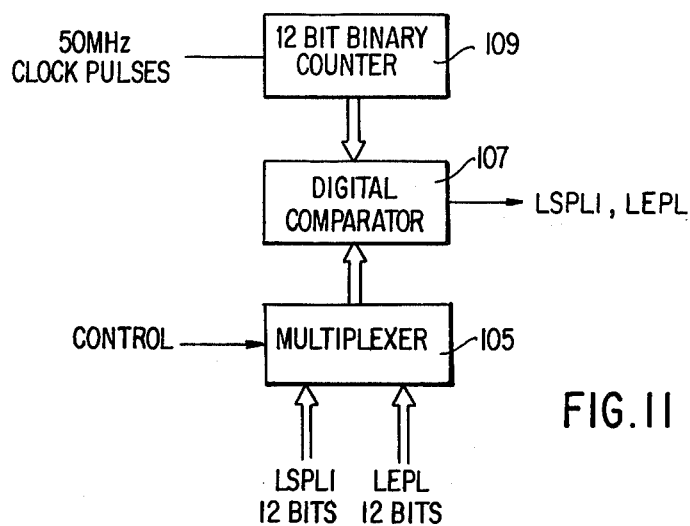
FIG. 11 is a block diagram for explaining the manner in which the positions of the sample and expectation points LSPL1 and LEPL, respectively are determined along a video scan line for the left border.
Figure 12:
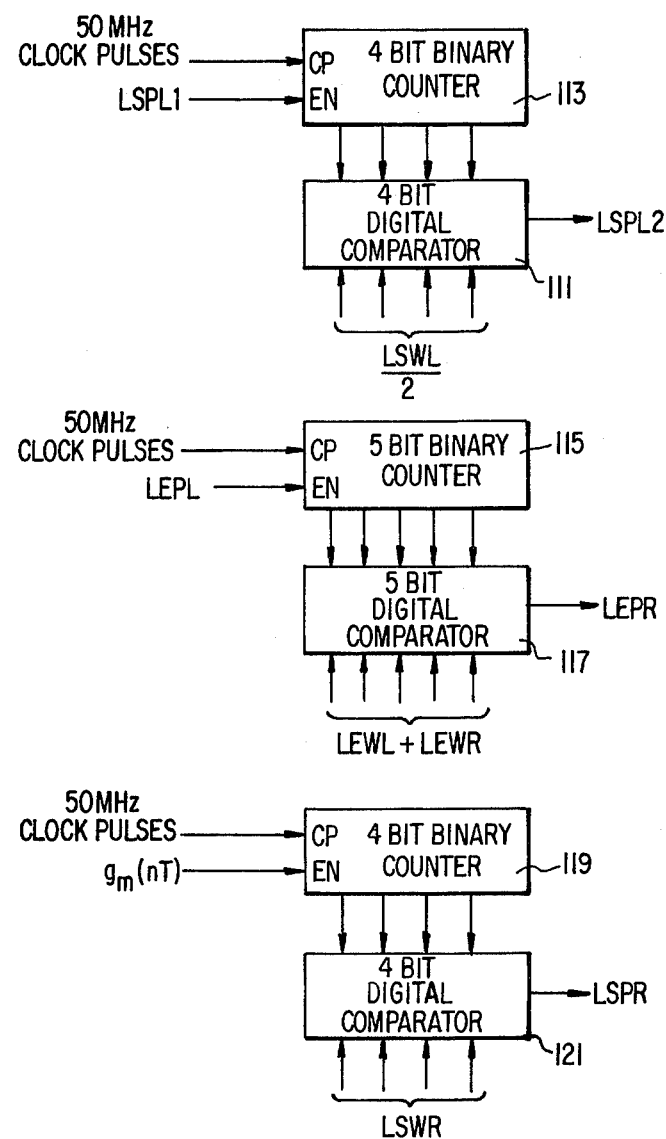
FIG. 12 is a block diagram for explaining the manner in which the positions of the sample points LSPL2 and LSPR, and the end point LEPR of the expectation window are determined along a video scan line for the left border.

The position of a border point is preferably determined in a 12-bit format by counting clock pulses from the rising edge of a horizontal sync pulse to this border point for the scan lines traversing the left ventricle; this is handled by the digital processor unit 41 which comprises the circuitry depicted in FIGS. 10, 11 and 12. This digital processor unit 41 then determines the center, as well as the beginning — and end point of the new expectation window for the second left border point by an algorithm based on the location of the preceding border point and on the location of the corresponding border points in the preceding one or two video fields and also determines the location of three sample points used for the calculation of the reference level for the next border point. After the expectation window and sample points have been calculated, the left border RAM 49 is updated at the appropriate address with the last detected border point. To determine the location of sample points and expectation window along a video scan line the count is compared with the appropriate data words supplied by the digital processor. Three track and hold circuits 51 each sample and hold for a certain time interval on a line by line basis the voltage level at a respective one of the three sample points defined by the digital processor unit 41. The set of voltage levels of the sample points is fed to the dynamic reference level analog computer circuit 45 which operates on them to generate, in accordance with another algorithm, a new reference level for the comparator 35, resulting in the detection of the second left border point within the defined expectation window. For the third and following left border points, the digital processor unit 41 can apply each of the four possible combinations of line and field extrapolation principles for the calculation of the new expectation window.

The right border subsystem 53 will now be described. With a short fixed delay after the first left border point 47 has been detected, an electronic generator 55 is started, simulating the aortic valve 29. Incorporation of the aortic valve simulation generator 55 is necessary because the automatic detection of this part of the ventricular outline is impossible due to the flow of contrast material into the aorta. The slope of the line representing the aortic valve 29 is also manually adjustable. Visual feedback resulting from the display of the X-ray picture on the screen of the TV monitor 27 together with the contour pulses, assists the operator in the operation of the device. When the "artificial valve" meets the right border, its generation is terminated while the expectation window for the first actual right border point is determined. An analog comparator 57 has a control input fed by the digital processor unit 59. The aortic valve simulation generator 55 is connected to the digital processor unit 59. Digital processor unit 59 is identical to digital processor unit 41 except that unit 59 has one additional input (on B-bus 85) to accommodate the output of aortic valve simulation generator 55. During the aortic valve simulation period the digital processor unit 59 determines the center of the expectation window from the position of the preceding border point in the current field plus a constant term which determines the slope of the simulated aortic valve. The reference level analog computer 61 applies a dc preset reference level to the analog comparator 57 during this period. If the analog comparator 57 does not encounter a point with the same brightness level as the preset reference level within the expectation window, then the end of the expectation window is defined as the contour point. However, if a point occurs with the correct reference level within the defined expectation window, then this point is defined as the first right border point 63 and the aortic valve simulation generator 55 is stopped. As the comparator 57 changes state a narrow pulse is fed to the summation amplifier, where it is mixed into the video signal for visual feedback purposes. Because of the sudden change in direction from the simulated valve to the actual right border, the digital processor unit 59 defines the center of the expectation window for the second right border point as having the same horizontal coordinate as the first right border point and also determines the location of three sample points. After these coordinates have been calculated, the right border RAM 65 is updated at the appropriate address with the last detected border point.

Three track and hold circuits 67 each sample and hold for a certain time interval on a line by line basis the voltage level at a respective one of the three sample points defined by the digital processor unit 59. The set of voltage levels of the sample points is fed to a dynamic reference level analog computer circuit 61, which operates on them to generate, in accordance with another algorithm, a new reference level for the comparator 57. As soon as the video signal which is fed to the analog comparator 57 from the video clamp 21 reaches the reference level calculated by the dynamic reference level analog computer circuit 61, the second right border point 69 is detected. For the third and following right border points, the digital processor unit 59 can apply each of the four possible combinations of line and field extrapolation principles for the calculation of the center of the expectation window.

Figure 3A:
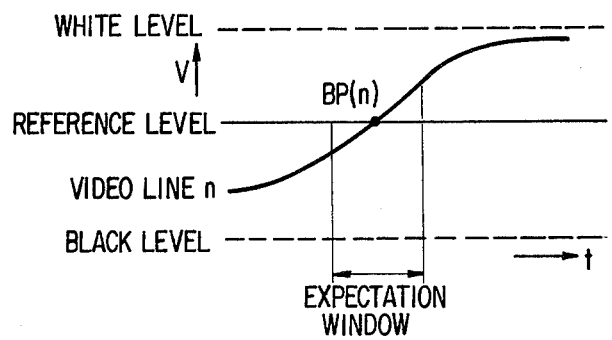
FIGS. 3A to 3C illustrate definition of the border points with respect to the expectation window.
Figure 3B:
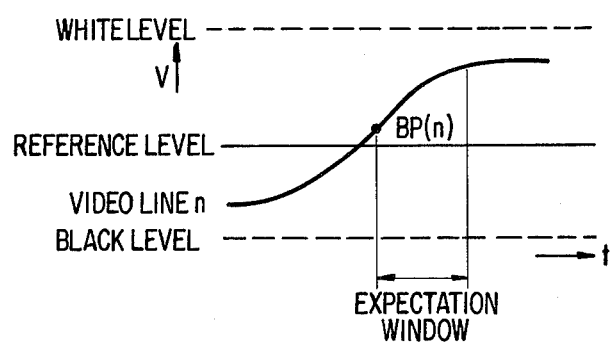
Figure 3C:
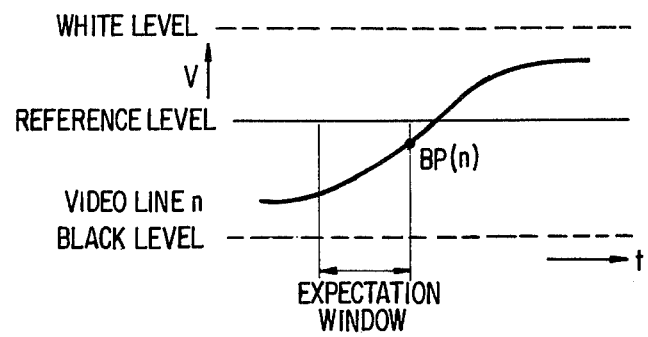

In the case where the video signal does not cross the reference level within the expectation window, forced border points are generated. This occurrence may be due to a sudden change in the video level at the border caused by intervening structures such as ribs or the diaphragm, or due to a sudden position change in the actual left ventricular border from previous border points. The possible situations are illustrated in FIG. 3 for the left border. FIG. 3(a) shows the normal situation for a border point that is detected within the expectation window. Consider now the case, as illustrated in FIG. 3(b), in which the actual contour has shifted to the left such that the video signal is already above the reference level at the beginning of the expectation window. A border point is then generated at the beginning of the expectation window as the comparator is enabled. FIG. 3(c) shows the case in which the actual border has shifted to the right such that the video signal is below the reference level during the entire expectation window period. This situation is recognized and a forced border point is then generated at the end of the expectation window.

The system is implemented so that no more than two contour points will occur on a video line traversing the left ventricle, one for the left border and one for the right border.

The contour detection is stopped and an outpulse 71 is generated by an outpulse circuit 73 connected to the computer interface 75 and the digital processor units 41, 59 as soon as the distance between the left and right border points is smaller than the adjustable ventricular apex 31 difference or if the left-hand side of the expectation window for the right border occurs before a left border point has been detected, thus avoiding continuation of the detection process for the remaining portion of the field.

The obtained border positions are transmitted from the analog comparators 35, 57 to a computer interface 75 of conventional design. The computer interface determines the coordinates of the left ventricular border as detected by the contour detector in an 8-bit format over a number of video fields selected by the operator and controls their transfer to the core memory of a digital computer 77, thereby permitting real time operation. For purposes of calculating size and shape of the left ventricle, it is sufficiently accurate to store each x-coordinate in an 8-bit format. The digital computer can be programmed to calculate the left ventricular volume from the detected border points using a known mathematical model.

Figure 4:
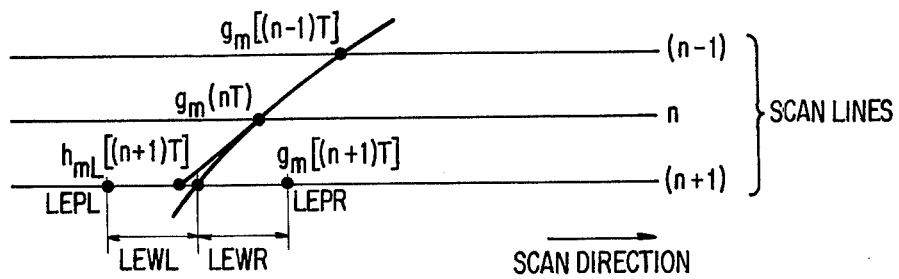
FIG. 4 is a diagram for explaining the manner in which the center of the expectation window is determined by the first order line extrapolation method.

The algorithm for determining the center of the expectation window will now be discussed with reference to FIGS. 4, 5, and 6. A border point is denoted as $g_m(nT)$, where $m$ refers to the field number and $n$ to the line number. Using a first order line extrapolation principle, the center of the expectation window $h_{mL}[(n+1)T]$ on line $(n+1)$ is derived from the previously detected border positions $g_m[(n-1)T]$ and $g_m(nT)$ on video lines $(n-1)$ and $n$, respectively. The new position is linearly extrapolated, as shown in FIG. 4. The position of $h_{mL}[(n+1)T]$ is calculated as $$h_{mL}[(n+1)T] = 2g_m(nT) - g_m[(n-1)T] \quad (1)$$

The distance from the left hand side (LEPL) of the expectation window to the center is denoted LEWL, the distance from the center to the right hand side (LEPR) is denoted LEWR, and T is the video scan line period. Right and left window widths are separately and manually adjustable. Using this linear extrapolation, the center of the window is generally taken as a good approximation of the next border point.

Figure 5:
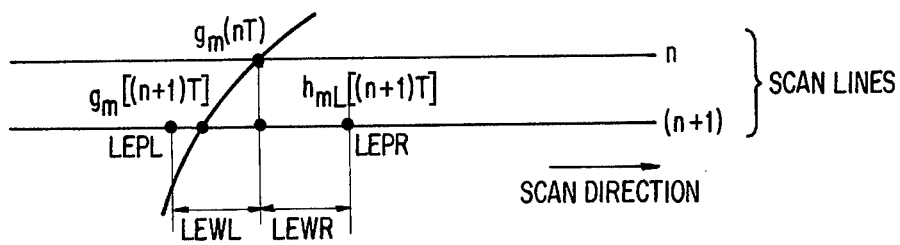
FIG. 5 is a diagram for explaining the manner in which the center of the expectation window is determined by the zeroth order line extrapolation method.

Under low contrast conditions, it is sometimes advantageous not to extrapolate but rather to assign the center of the expectation window on line $(n+1)$ the same x-coordinate as the last detected border point on line $n$, as illustrated in FIG. 5. This is referred to as the zeroth-order line extrapolation principle, and can be written as $$h_{mL}[(n+1)T] = g_m(nT) \quad (2)$$

Because the border position changes very little from field to field, the center of the expectation window in the current field can also be approximated by linearly extrapolating corresponding border points in the previous two fields. This is referred to as the first order field extrapolation principle.

To calculate the center of the expectation window using the first order field extrapolation principle, one must distinguish between even and odd fields. Assuming field $m$ is an odd field, the center of the expectation window is defined as $$h_{mF}[(n+1)T] = 2g_{(m-1)}(nT) - g_{(m-2)}[(n+1)T] \quad (3)$$

If field $m$ is an even field, $h_{mF}[(n+1)T]$ is defined as $$h_{mF}[(n+1)T] = 2g_{(m-1)}[(n+1)T] - g_{(m-2)}[(n+1)T] \quad (4)$$

The zeroth order field extrapolation principle takes only the last field into account. Applying both the line and field extrapolation principles simultaneously, the center of the expectation window $h_m[(n+1)T]$ on line $(n+1)$ in the current field $m$ is then defined as the average position of the centers of the expectation windows determined separately by the line and field extrapolation methods. This results in:

Field $m$ is odd field:

$$h_m[(n+)T] = \frac{2g_m(nT) - g_m[(n-1)T] + 2g_{(m-1)}(nT) - g_{(m-2)}[(n+1)T]}{2} \quad (5)$$

Field $m$ is even field:

$$h_m[(n+1)T] = \frac{2g_m(nT) - g_m[(n-1)T] + 2g_{(m-1)}[(n+1)T] - g_{(m-2)}[(n+1)T]}{2} \quad (6)$$

The zeroth order field extrapolation principle can be applied by substituting $g_{(m-1)}(nT)$ and $g_{(m-1)}[(n+1)T]$ in equations (5) and (6) respectively, instead of $g_{(m-2)}[(n+1)T]$.

Figure 6:
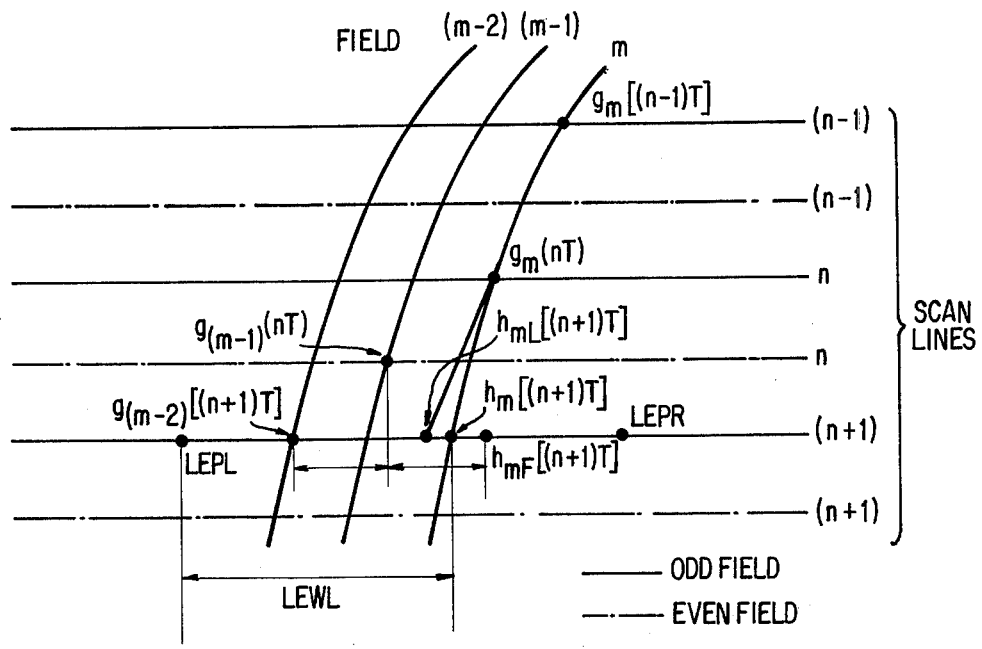
FIG. 6 is a diagram for explaining the manner in which the center of the expectation window is determined by the first order line and field extrapolation methods.

The determination of the center of the expectation window using the first-order line and field extrapolation principles is illustrated in FIG. 6. The center of the expectation window can thus be determined in four different ways by selecting independently the zeroth- and first-order line and field extrapolation principles, respectively.

Figure 7:
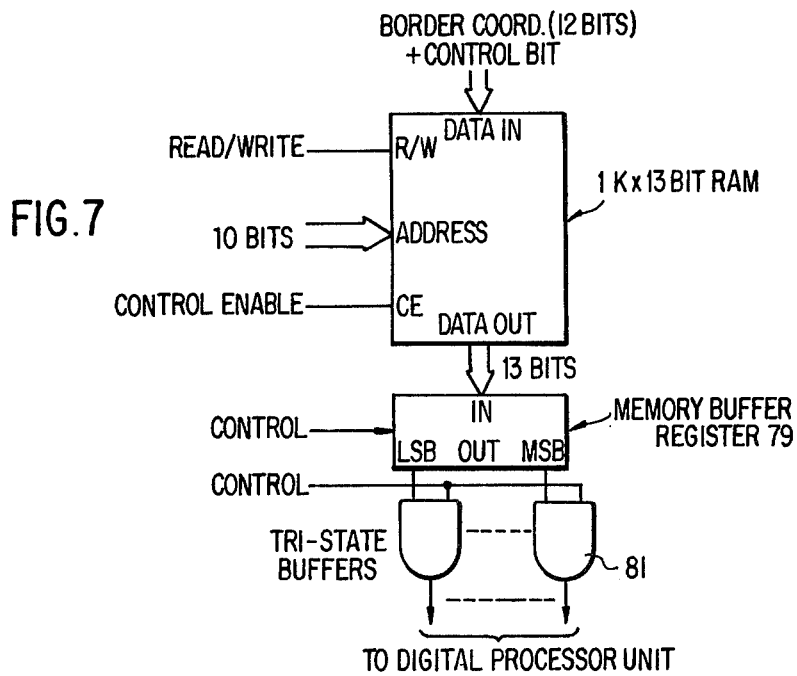
FIG. 7 is a diagram showing the memory configuration for storing the left-border coordinates of two fields.

A random access field memory 49 is included in the left border subsystem for the storage of the 12-bit coordinates, plus a control bit, from the last two fields which have been processed. An identical memory 65 is included in the right border subsystem. The memories are updated with each newly detected border point in the current field, and feed the associated digital processor unit 41 or 59 for determination of the center of the expectation window by the field extrapolation method. The memory configuration for storing the left border coordinates is illustrated in FIG. 7. With each coordinate available in a 12-bit format, the thirteenth bit is used as a control bit, which is zero, if there is no border point on a scan line and one if there is a border point. Storing the 13 bits present at the DATA IN input at a location specified by a 10-bit address whose eight least significant bits are determined by counting the scan lines during a video field, whose 9th bit is always zero, and whose most significant bit can be 0 or 1 depending on whether one wants to access the coordinates of an odd or even field respectively, is accomplished by having the READ/WRITE and CONTROL ENABLE inputs both low. Reading data from a specified memory location occurs when the READ/WRITE input is high and the CONTROL ENABLE low. After the DATA OUT outputs have stabilized, these data can be loaded into the memory buffer register 79. Using tri-state buffers 81, this information can be applied to the associated digital processor unit during the appropriate time periods to calculate the center of the expectation window.

Figure 8A:
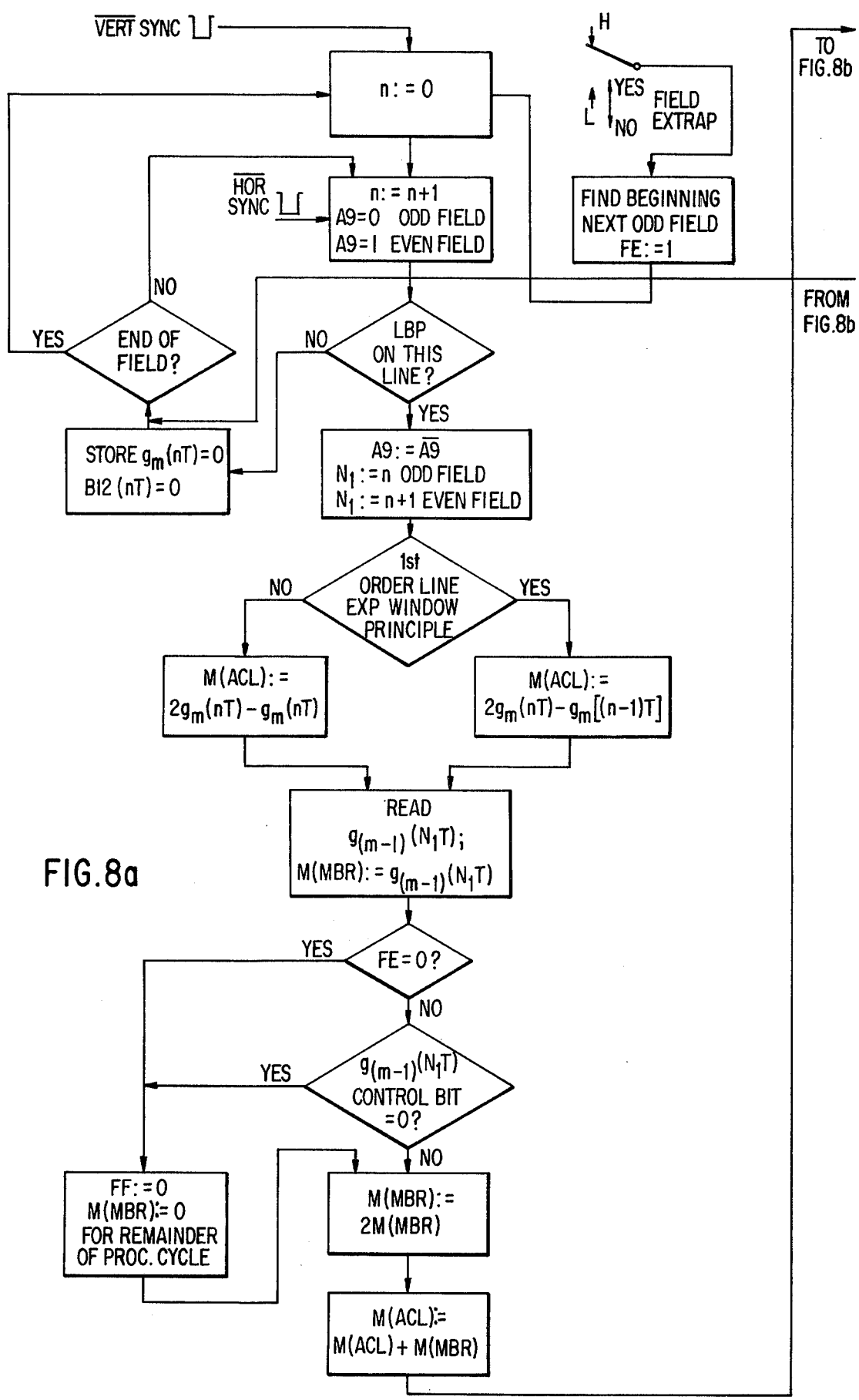
FIGS. 8A and 8B are a flow chart for calculating the center of the expectation window by the line and field extrapolation methods.
Figure 8B:
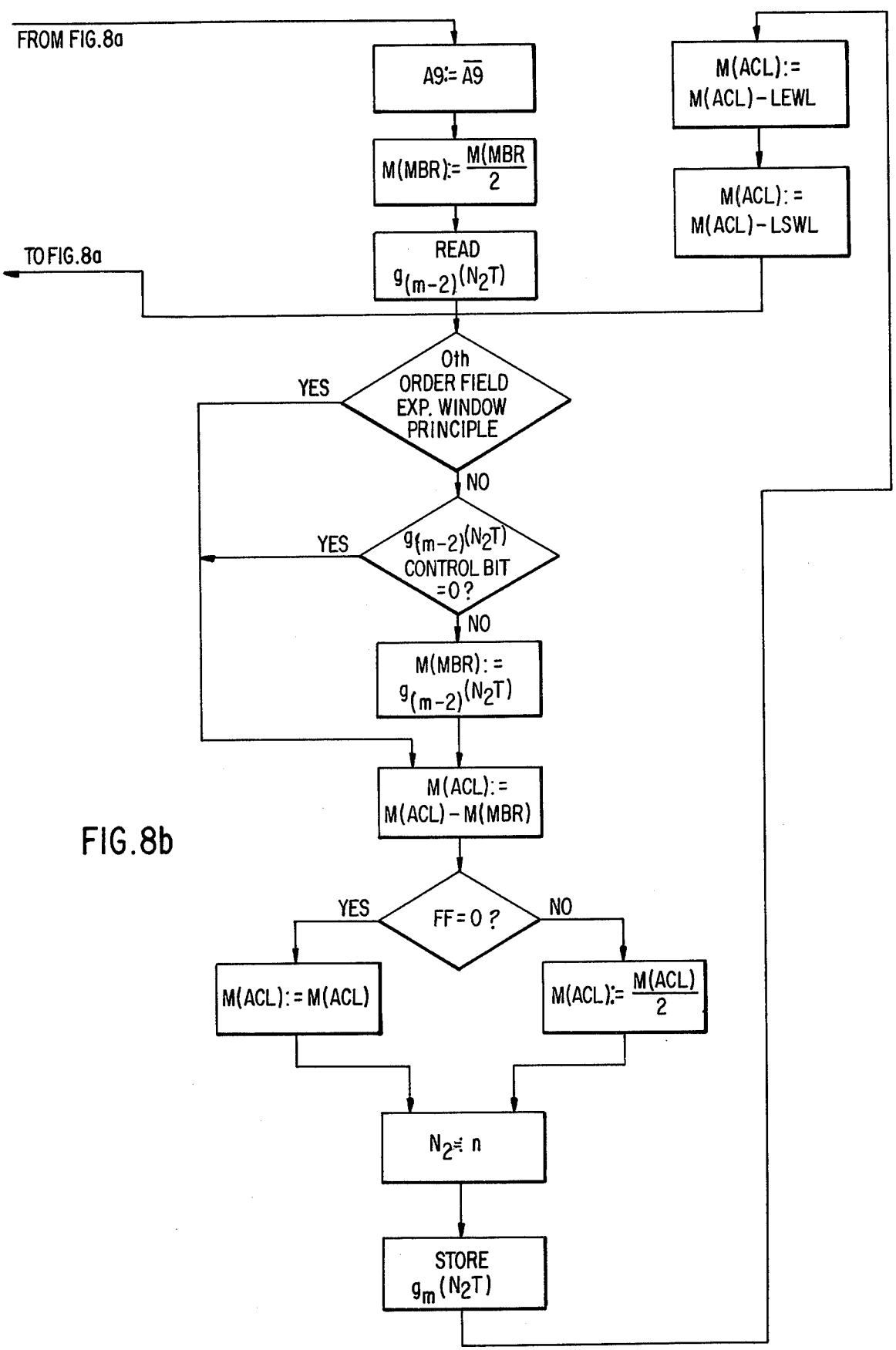

FIG. 8 is a flow chart of the procedure used to calculate the center of the expectation window for the left border on line $(n+1)$ in field $m$. The processing cycle is divided into 11 time states by digital processor unit 41 and the time states are designated ts0 through ts10.

The field extrapolation principle is enabled by activating a switch shown at the top of the flow diagram. So long as this switch has not been activated, the center of the expectation window is determined using the line extrapolation principle only (this will be clarified later on). To always start in the same phase after having activated the switch, the first complete odd field after this moment is defined as the first field with FE (field enable) = 1. The most significant address bit A9 is made low at the beginning of each video line in an odd field to access the lower half of the memory 49 and is made high at the beginning of each video line in an even field. The first full line in a field after the occurrence of the vertical synchronization pulse is assigned the value $n = 1$.

The calculation of the center of the expectation window $h_m[(n+1)T]$ is only carried out if a left-border point has been detected at the current line $n$. If no left-border point has been detected during a scan line, then $g_m(nT) = 0$ is stored into memory 49 with a corresponding control bit equal to zero, indicating that all zeros have been stored at this location. As a result, all scan lines not traversing the left ventricle are assigned a control bit equal to zero. Because of the vertical movement of the entire left ventricle over a heart cycle plus its contraction and ejection movements, it is important to know if actual contour points were detected at the selected video lines in the previous fields.

Assuming a left-border point has been detected, the most significant address bit is inverted at the beginning of time-state ts0 to access the border coordinate in the previous field. Also, a 1 is added to the address if the current field is an even field (compare eqs. (3) and (4)). During time state ts1, the center of the expectation window is calculated according to the line extrapolation principle as $2g_m(nT)-g_m[(n-1)T]$. This calculation is done in the digital processor 41. The result is stored in a 16 bit register 87 (FIG. 10) of the same type as used for the memory buffer register 79. This 16-bit register is referred to as ACL (accumulator left border) and its contents as M(ACL); therefore, $$M(ACL) = 2g_m(nT)-g_m[(n-1)T]$$

If the zeroth-order line extrapolation is selected, $g_m(nT)$ is substituted for $g_m[(n-1)T]$ and the result is $$M(ACL) = 2g_m(nT) - g_m(nT) = g_m(nT)$$

The field memory 49 is enabled at the beginning of time state ts1 and, with the correct address applied, $g_{(m-1)}(N_1T)$ is read and stored into the memory buffer register at the end of ts2, that is $$M(MBR) = g_{(m-1)}(N_1T)$$

where $N_1 = n$ if the current field is an odd field and $N_1 = n + 1$ for an even field. At the end of ts2, it is also checked if the field extrapolation principle was not selected (FE=0?) and if the control bit for $g_{(m-1)}(N_1T)$ is equal to zero. If the answer to one or both of these questions is true, then the MBR is cleared for the remainder of this processing cycle. This situation is referred to as FF:=0. This means that the center of the expectation window will be determined only by the line extrapolation principle. Independent of whether the data in the MBR are unequal to zero or not, the contents of MBR are shifted over one position to the right at the end of ts3, which yields M(MBR): = 2M(MBR). These new data are added to the contents of the accumulator during ts4. Assuming that one had selected the first-order line extrapolation principle and activated the field extrapolation switch, the contents of ACL would be $$M(ACL) = 2g_m(nT)-g_m[(n-1)T]+2g_{(m-1)}(N_1T)$$

At the beginning of ts3, the address is set for the reading of the data from field $(m-2)$ during a later time state. The most significant address bit A9 is again inverted, thus giving it the initial value it had at the beginning of the video line, and a 1 is added to the current line number. The next step during ts5 is to shift the data in the MBR one position to the left, resulting again in $$M(MBR) = g_{(m-1)}(N_1T)$$

Meanwhile, the coordinate $g_{(m-2)}[(n+1)T]$ is read from memory 49, but not yet loaded into the MBR. At the end of ts5, the system checks whether the zeroth-order field extrapolation principle was selected and whether the control bit for $g_{(m-2)}[(n+1)T]$ is equal to zero. If the answer to one or both of these checks is true, then the zeroth-order field extrapolation will be applied. The border coordinate $g_{(m-2)}[(n+1)T]$ will not be stored in the MBR, but the old data $g_{(m-1)}(N_1T)$ are subtracted from the accumulator contents during ts7. If this is not the case, then $g_{(m-2)}[(n+1)T]$ is stored in the MBR at the end of ts2 and the contents of MBR are subtracted from the accumulator contents.

Earlier, the conditions were described for which the MBR was cleared for the remainder of the processing cycle (FF = 0). It is clear that, under these conditions, the contents of MBR do not change even if one wants to load $g_{(m-2)}[(n+1)T]$, because MBR remains cleared independently of the clock pulse.

These same conditions are also important for the next step. If FF=0, the accumulator contains the center of the expectation window calculated according to the line extrapolation principle only. For this condition, the clock to the accumulator is inhibited during ts8 and nothing happens. If FF $\neq$ 0, then the accumulator contains the sum of the centers of the expectation windows as calculated according to the line and field extrapolation principles separately. To obtain the average of these centers, the contents of the accumulator are shifted one position left during ts8, resulting in $$M(ACL) = h_m[(n+1)T]$$

At the beginning of ts7, the extra 1 in the memory address is removed and the last detected border point $g_m(nT)$ is stored in memory during ts8 and ts9.

The expectation window width LEWL is subtracted from $h_m[(n+1)T]$ during ts9 and the result is stored in the accumulator. These data are also stored in D flip flop registers; the contents of these registers then represent the left-hand side LEPL of the expectation window. Similarly, the sample window width LSWL is subtracted from the contents of the accumulator during ts10 and stored in ACL at the end of ts10. The final result is then that the accumulator contains the position of LSPL1 for the next video line in the current field.

The processing cycle is now complete and we return to the beginning of the flow chart for the next processing cycle. If line $n$ was not the last line in the video field, then the address is incremented by one and bit A9 is reset to zero if the current field is an odd field and set to one for an even field. With $n$ being the last line in the field, the line counter is reset during the vertical synchronization pulse and the whole cycle is repeated.

A digital processor unit 41, 59 is included in the system for the calculation of the center, the beginning and end points of the expectation window and the positions of the sample points.

Formulas (5) and (6) are given for the general case that the center of the expectation window is determined using both the first-order line and field extrapolation principle. The zeroth-order line extrapolation principle can be applied by substituting $g_m(nT)$ for $g_m[(n-1)T]$ at the time of calculation. Similarly, the zeroth-order field extrapolation principle can be applied by substituting $g_{(m-1)}(nT)$ and $g_{(m-1)}[(n+1)T]$ in equations (5) and (6) respectively, for $g_{(m-2)}[(n+1)T]$. With each border position known in a 12-bit format, the center of the expectation window is also determined in a 12-bit format, applying formulas (5) and (6). However, we also must determine the beginning and end points of the expectation window to enable the comparator, and the sample points to calculate the dynamic reference level.

If it is assumed for simplicity, that only the first-order line extrapolation principle is applied, the beginning and end points of the expectation window on line $(n+1)$ are shown in FIG. 4 for the left border. These points are denoted LEPL and LEPR, respectively. According to the way the system has been implemented, these beginning and end points are defined as $$\text{LEPL} = h_m[(n+1)T] - \text{LEWL} \qquad (7)$$

and $$\text{LEPR} = \text{LEPL} + \text{LEWL} + \text{LEWR} \qquad (8)$$

that is, LEPR is determined from the position of LEPL.

Figure 9:
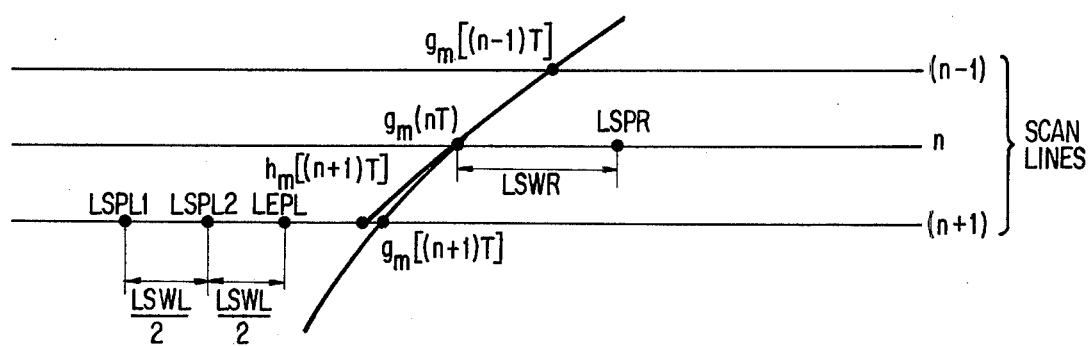
FIG. 9 is a diagram for explaining the manner in which three sample points are defined for the determination of the reference level for the next line for the left border.

Three sample points are defined for the left border as illustrated in FIG. 9. The sample points are denoted LSPR, LSPL1 and LSPL2, respectively. Assuming the last detected border point is $g_m(nT)$ on line $n$, the video signal is sampled on the same line inside the ventricle at a distance LSWR from $g_m(nT)$ and on the next line $(n+1)$ in the background area at distances LSWL and LSWL/2 before the left-hand side of the expectation window LEPL, respectively. The video samples at the three defined sample points are used to calculate the reference level for line $(n+1)$. FIG. 9 clearly shows that the position of the sample points LSPL1 and LSPL2 are determined with respect to the center of the expectation window, thereby taking into account the local direction and movement of the left ventricular outline. This results in a more accurate determination of the reference level for the next border point.

In formulas:
Sample point LSPR is determined from the detected border point $g_m(nT)$ on line $n$ as $$\text{LSPR} = g_m(nT) + \text{LSWR} \qquad (9)$$

and sample point LSPL1 is calculated from LEPL as $$\text{LSPL1} = \text{LEPL} - \text{LSWL} \qquad (10)$$

In the implemented system, sample point LSPL2 is derived from LSPL1 as $$\text{LSPL2} = \text{LSPL1} + \text{LSWL}/2 \qquad (11)$$

The selected window widths LEWL, LEWR, LSWL and LSWR are available in binary format.

The digital processor unit 41 comprises the subsystems shown in FIGS. 10, 11 and 12 and functions to determine the center, the beginning and end points of the expectation window and the positions of the sample points. These subsystems are described in more detail in the following paragraphs.

The digital processor unit 41 contains an arithmetic unit as shown schematically in FIG. 10 for the left border.

Using tri-state buffers, the addends are all applied to the A-bus 83, and the augends or subtrahends to the B-bus 85. The result of an arithmetic addition or subtraction is stored in the accumulator ACL 87 and can be applied again to the A-bus for the next arithmetic operation.

After the left border point $g_m(nT)$ has been detected, its 12-bit coordinate is available at the inputs of the register 89 and buffer 91. Consider the case when the zeroth-order line extrapolation principle is selected. At the start of time-state ts1, the 12 bits are stored in the register 89. With the tri-state buffers 91 and 93 enabled during ts1, 2 $g_m(nT)$ is applied to the A-bus 83 and $g_m(nT)$ to the B-bus 85 (the multiplication by two has been achieved by shifting the buffer output one bit position on the bus). The Arithmetic Logic Unit 95 (ALU) control being set for subtraction, the resulting 2 $g_m(nT)$ - $g_m(nT)$ is stored at the end of ts1 into the accumulator ACL 87.

For the first-order line extrapolation principle, 2 $g_m(nT)$ is again applied to the A-bus 83 during ts1 through buffer 91. However, at this moment, $g_m(nT)$ is not stored in the register 89; during ts1 the information in this register is then still $g_m[(n-1)T]$ from the previous line and this coordinate is applied to the B-bus 85. At the end of ts1, the resulting 2 $g_m(nT)$ - $g_m[(n-1)T]$ is stored in the accumulator 87.

The contents of the accumulator 87 can be applied to the A-bus 83 at the appropriate time states as defined in FIG. 8 for additional additions and subtractions. The data from the left border RAM 49 is applied to the B-bus through the buffer 97.

The binary word representing LEWL is applied to buffer 99 and the binary word representing LSWL to buffer 101. This allows the calculation of LSPL1 and LEPL. After the position of LEPL has been calculated it is stored in register 103. At the end of the processing cycle, the position of LSPL1 is stored in the accumulator 87.

The position determination of these points on a scan line is also performed in the digital processor unit and is described with the block diagram of FIG. 11. The data stored in the ACL 87 and register 103, representing LSPL1 and LEPL respectively, are connected to the multiplexer 105. From the beginning of a scan line until the position of LSPL1 has been determined, the multiplexer control is set such that the 12 bits representing LSPL1 are applied to one side of the 12 bit comparator 107. The other side of the comparator is connected to the outputs of a 50 MHz counter 109. This counter 109 starts counting the clock pulses at the end of the horizontal sync pulse for the scan lines traversing the left ventricle. As soon as the contents of the counter 109 equal the 12-bit data word for LSPL1; the output of the comparator 107 becomes logically high, indicating the position of LSPL1. The multiplexer control is now changed such that the 12 bits for LEPL are applied to the digital comparator 107, whose output becomes logically low again. The counter 109 continues to count and the output of the comparator 107 becomes high again as the state of the counter 109 equals the 12-bit data word for LEPL. This initiates the enabling of the analog comparator 35. As the video signal crosses the reference level, the analog comparator 35 changes state and the counter 109 stops counting clock pulses. The state of the counter 109 thus represents the new border coordinate on this particular line.

The position determination of the points LSPL2, LEPR and LSPR are also performed in the digital processor unit and are described with the block diagrams in FIG. 12. For the position determination of LSPL2, the 4 bits representing LSWL/2 are applied to one side of a 4 bit digital comparator 111 and the outputs from a 4-bit counter 113 to the other side. This 50 MHz counter is enabled as soon as LSPL1 has been detected. The counter 113 then starts counting until its state equals LSWL/2, so that the output of the comparator 111 becommes high indicating the position of LSPL2. The position determination of the points LEPR and LSPR are performed in identical ways. For LEPR, a 5-bit counter 115, connected to a 5-bit comparator 117, is enabled by LEPL and the counter 115 keeps on counting until its state equals LEWL + LEWR, which is applied to the other side of the comparator 117. If the analog comparator 35 did not detect a border point within the expectation window, then the comparator 35 is disabled at this moment, resulting in the generation of a forced border point at the end of the expectation window. For LSPR, a 4-bit counter 119, connected to a 4-bit comparator 121, is enabled by $g_m(nT)$ — that is the detected border point on this particular line — and the counter keeps on counting until its state equals LSWR, which is applied to the other side of the comparator 121.

The way the expectation and sample points for the right border are determined in the digital processor unit 59 are equivalent to the way described above for the left border. However, for the right border we also have to include the aortic valve generation, so that the processor unit includes one more input of B-bus 85 (FIG. 10) to accommodate the output of aortic valve simulation generator 55. The equations for the right border points are described below.

Figure 13:
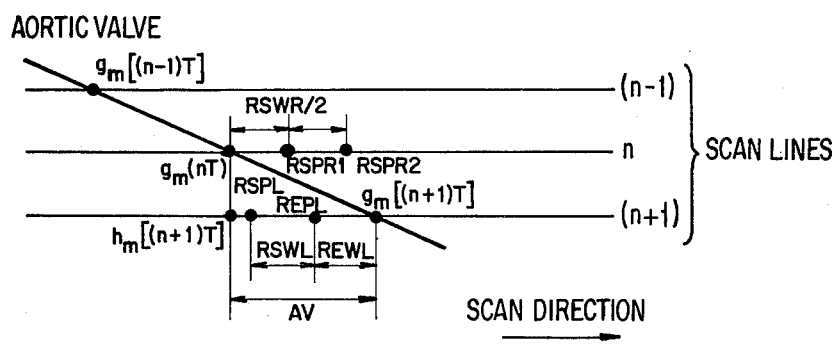
FIG. 13 is a diagram for explaining the manner in which the expectation and sample points for the right border are defined during the aortic valve simulation period.

The positions of the expectation and sample points during the aortic valve simulation are given in FIG. 13. So long as this simulated valve plane is generated, the field extrapolation principle is inhibited and only the zeroth-order line extrapolation principle is applied, necessary for the generation of a straight line.

The beginning point REPL of the expectation window on line $(n+1)$ is determined by $$REPL = g_m(nT) + AV - REWL \quad (12)$$

where Av is the aortic valve width, given in an 8-bit format. The end point of the expectation window during the aortic valve plane generation is defined as $$REPR = REPL + REWL \quad (13)$$

Sample point RSPL is defined as $$RSPL = g_m(nT) + AV - REWL - RSWL = REPL - RSWL \quad (14)$$

Sample points RSPR1 and RSPR2 on line $n$ are derived from $g_m(nT)$ as $$RSPR1 = g_m(nT) + RSWR/2 \quad (15)$$

and $$RSPR2 = g_m(nT) + RSWR \quad (16)$$

The general formulas for the expectation and sample points after the aortic valve simulation period can be derived from formulas (12), (13) and (14). For the general case with the center of the expectation window denoted $h_m[(n+1)T]$, equation (12) becomes $$REPL = n_m[(n+1)T] + AV - REWL \quad (17)$$

The end point REPR is defined as $$REPR = REPL + REWL + REWR \quad (18)$$

Equation (14) can now be written as $$RSPL = h_m[(n+1)T] + AV - REWL - RSWL \quad (19)$$

The formulas for RSPR1 and RSPR2 remain, of course, unchanged. In order that the timing for the right border arithmetic unit remains unchanged, the term AV is always included, but is made equal to zero outside the aortic valve simulation period.

Next the algorithm for dynamically adjusting the reference level according to local brightness levels on a line by line basis will be discussed. The brightness level changes along a border because of shading, nonhomogeneous distribution of the contrast agent in the left ventricle, and overlapping of Roentgen shadows from other organs and structures, such as diaphragms and ribs. Three sample points have been defined in FIG. 9 for the left border.

The reference level for the border point on line $(n+1)$ is then calculated as $$V_{ref}(n+1) = \frac{\alpha}{2}\left(VR + \frac{VL1}{2} + \frac{VL}{2}\right) + V_c \quad (20)$$

where $\alpha$ is a proportionality factor, $V_c$ is a constant voltage level, VR is the video sample at LSPR, and VL1 and VL2 the video samples at LSPL1 and LSPL2, respectively. By taking the average value of VL1 and VL2, either side of the contour has the same weight. The function of the two sample points at the background area will be explained later.

Figure 14:
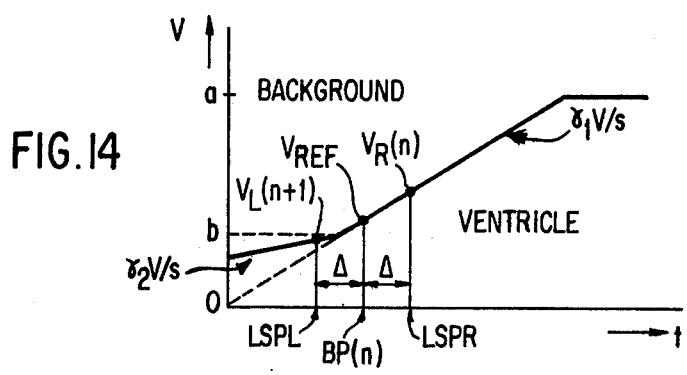
FIG. 14 illustrates the line periodic border model for the left border.

The behavior of the detection process can be analyzed by assuming a line periodic video signal, as shown in FIG. 14 for the left border. In order to simplify the calculations, one left sample point LSPL is assumed and both sample points LSPL and LSPR have the same distance $\Delta$ to the border point. With the slope of the video signal within the ventricle denoted by $\gamma_1$ V/s and in the background area by $\gamma_2$ V/s (with $\gamma_2 < \gamma_1$), and, assuming $b/\gamma_1 < BP(n) < b/\gamma_1 + \Delta$, the final value of the reference level can be calculated as $$V_{ref} = \frac{\frac{\alpha}{2}(\Delta\gamma_1 + b)(1 - \frac{\gamma^2}{\gamma^1}) + V_c}{1 - \frac{\alpha}{2}(1 + \frac{\gamma^2}{\gamma^1})} \quad (21)$$

A border point is said to be acceptable if it occurs on the ventricular slope within a distance Δ from the knee in the border model. This results in one sample point in the background area and the other on the ventricular slope.

The requirement for the reference level is then $$b < V_{ref} < b + \Delta\gamma_1 \qquad (22)$$

Solving (21) and (22) yields $$\frac{b - V_c}{\frac{\Delta}{2}(\gamma_1 - \gamma_2) + b} < \alpha < 1 - \frac{V_c}{b + \Delta\gamma_1} \qquad (23)$$

A practical value for $\alpha$ is 0.8 to 0.9, and for the distance Δ, approximately 0.5 us.

Using the linearized border model of FIG. 14 it can be theoretically derived that the optimum relation between $\alpha$ and $V_c$ under varying parameters $\gamma_1$, $\gamma_2$, and $b$ is $$V_c = b_{MIN}(1 - \alpha) \qquad (24)$$

where $b_{MIN}$ is the lowest knee level in the image. Approximating $b_{MIN}$ in the current field with the measured $(VL1/2 + VL2/2)_{MIN}$ of the previous field and applying equation (24) then only requires an adjustment of the $\alpha$ factor for the appropriate $V_{ref}$ as determined according to equation (21).

The two sample points LSPL1 and LSPL2 are important in areas of low contrast where the actual video signal may be different from the assumed border model. At those places, it often occurs that the slope $\gamma_2$ becomes negative, resulting in a too high reference level, as calculated from equation (20). This situation is characterized by VL1>VL2 and is recognized in the system. Under this condition, an error term $V_{error}$ = VL1/2 - VL2/2 is determined and subtracted from the term VL1/2 + VL2/2 in the formula for the reference level. The effect is that the reference level is determined as if the border signal had a background slope of $\gamma_2 = 0$. On these bases, the final formula for the reference level can be written as $$V_{ref} = \frac{\alpha}{2}\left(\frac{VL1}{2} + \frac{VL2}{2} - V_{error} + VR\right) + V_c \qquad (25)$$

where $$V_{error} = \frac{VL1}{2} - \frac{VL2}{2}, \text{ if } \frac{VL1}{2} > \frac{VL2}{2}$$

$$= 0, \qquad \text{if } \frac{VL1}{2} < \frac{VL2}{2}.$$

Figure 15:
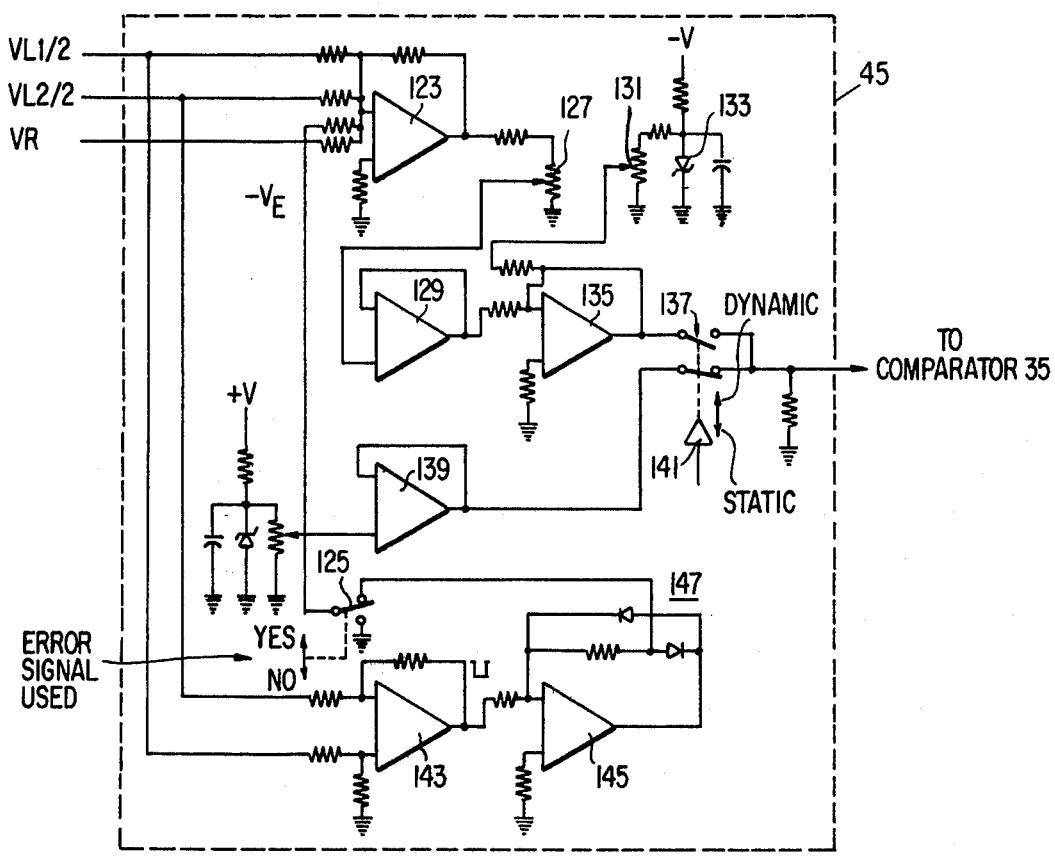
FIG. 15 is a detailed circuit diagram of the dynamic reference level analog computer circuit.

Referring to FIG. 15, there is shown a detailed circuit diagram of the dynamic reference level analog computer circuit 45 for operating on the sample points LSPR, LSP1, and LSPL2 to generate a reference level for the analog comparator 35.

The video samples $V_R$, VL1/2, and VL2/2, and the negative error signal are applied to the negative input of the operational amplifier 123 which is used as a −1 amplifier. The signals VL1/2 and VL2/2 at half the amplitude of the original signal can be obtained by use of an accurate voltage divider (not shown). The output of amplifier 123 is the negative of the sum of these signals. The error term is or is not included, depending on the setting of the switch 125. The $\alpha/2$ factor in the formula for the reference level is implemented with a resistive divider 127. The voltage follower operational amplifier 129 acts as a buffer and its output signal equals the product of $\alpha/2$ and the output of amplifier 123 where $0 < \alpha < 1$. The negative adjustable level of $-V_c$ volts is obtained with a potentiometer 131 connected to a zener diode 133 stabilized reference voltage. The $-V_c$ volts and the output signal from amplifier 129 are applied to the negative input of the operational amplifier 135 which is used as a −1 amplifier. The output of this amplifier then equals the negative of the sum of the latter two signals which is the required dynamic reference level. This signal is connected to one of the inputs of a single-pole, double-throw junction FET switch 137. Depending on the state of the switch, the output is then either the dynamic reference level or the output signal from the operational amplifier 139, which provides an adjustable DC level. This DC level is applied when a constant reference level is selected for the border detection and for the detection of the first left-border point when the dynamic reference level mode is selected. The desired switch setting is achieved by applying the appropriate logic signal at the input of the high-speed switch driver 141.

The error term is generated with the operational amplifiers 143 and 145. The sampled video level VL1/2 is applied to the positive input of the operational amplifier 143 and VL2/2, to the negative input. The operational amplifier 143 is used as a difference amplifier, resulting in an output voltage equal to the difference of the latter two signals. When (VL1/2) exceeds (VL2/2) is determined by use of the precision limiter circuit 147. With the positive input of amplifier 145 connected to ground, the output of the precision limiter is just the required error signal.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A real-time contour detector and data acquisition system for an angiographic apparatus having video scan means for converting X-ray images of a cardiac chamber characterized by a change in brightness level compared with its surrounding into video format and displaying the X-ray images in recurring video fields and comprising:

sampling means adapted to be coupled to the video scan means for sampling the brightness level of predetermined sample points of the current video field in the region of the last detected border point;

reference level means connected to the sampling means and responsive to the sampling of the brightness level of the predetermined sample points for generating a reference brightness level at which the next border point can be detected;

comparator means connected to the reference level means for comparing the brightness level along a video scan line in the current video field with that of the reference brightness level to detect the next border point;

field memory means for storing the coordinates of detected border points from two preceding video fields;

processor means connected to the comparator means, the field memory means, and the sampling means for enabling the comparator means only within a narrow expectation window on the next video scan line centered about the expected next border position and for determining the sample points to be sampled by the sampling means; and data acquisition means connected to the comparator means for acquiring the detected border points.

2. The system recited in claim 1 wherein the reference level means generates a reference level representative of $$\frac{\alpha}{2}\left(\frac{VL1}{2} + \frac{VL2}{2} - V_{error} + VR\right) + V_c$$

where
α is a proportionality factor,
$V_c$ is a constant voltage level,
VR is a voltage sample corresponding to a point within said cardiac chamber,
VL1 and VL2 are voltage samples corresponding to points in said surrounding, and $$V_{error} = \frac{VL1}{2} - \frac{VL2}{2}, \text{ if } \frac{VL1}{2} > \frac{VL2}{2}$$
$$= 0, \qquad \text{if } \frac{VL1}{2} < \frac{VL2}{2}.$$

3. The system described in claim 1 wherein the reference level means generates a reference level which is a function of the brightness of a sample point within said cardiac chamber and the brightness at two sample points outside said cardiac chamber, the position of said outside sample points being established with respect to the center of said expectation window so as to take into account the local direction and movement of the cardiac chamber contour.

4. The system as set forth in claim 1 wherein means are included for generating a forced border point if the brightness level encountered during the period of the expectation window fails to exceed said reference brightness level.

5. The system recited in claim 1 wherein means are included for generating a forced border point when the brightness level encountered at the onset of the expectation window exceeds said reference brightness level.

6. A system as claimed in claim 1 wherein said processor means determines the coordinates of the narrow expectation window for the next border point as a function of the location of the detected border points of at least one preceding video line in the current video field.

7. A system as recited in claim 1 wherein said processor means determines the coordinates of the narrow expectation window for the next border point as a function of the location of the corresponding border point in at least one preceding video field and as a function of the location of the detected border point in at least one preceding video line of the current video field.

8. The system set forth in claim 1 wherein said processor means determines the coordinates of a set of sample points as a function of the location of the last detected border point and the location of the center of the narrow expectation window for the next border point.

* * * * *